(12) United States Patent
Schader et al.

(10) Patent No.: US 11,324,895 B2
(45) Date of Patent: May 10, 2022

(54) FEEDBACK MECHANISM FOR AN INJECTION DEVICE

(71) Applicant: Sanofi-Aventis Deutschland GMBH, Frankfurt am Main (DE)

(72) Inventors: Marc Schader, Frankfurt am Main (DE); Michael Kneip, Frankfurt am Main (DE); Matthias Rau, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 290 days.

(21) Appl. No.: 16/346,250

(22) PCT Filed: Oct. 12, 2017

(86) PCT No.: PCT/EP2017/076056
§ 371 (c)(1),
(2) Date: Apr. 30, 2019

(87) PCT Pub. No.: WO2018/082887
PCT Pub. Date: May 11, 2018

(65) Prior Publication Data
US 2020/0046904 A1    Feb. 13, 2020

(30) Foreign Application Priority Data
Nov. 1, 2016 (EP) .................... 16196676

(51) Int. Cl.
*A61M 5/315* (2006.01)
*A61M 5/142* (2006.01)
(Continued)

(52) U.S. Cl.
CPC ...... *A61M 5/3157* (2013.01); *A61M 5/14248* (2013.01); *A61M 5/2033* (2013.01);
(Continued)

(58) Field of Classification Search
CPC .............. A61M 5/3157; A61M 5/2033; A61M 2005/2086; A61M 2205/581; A61M 5/1452
See application file for complete search history.

(56) References Cited

U.S. PATENT DOCUMENTS

| 5,630,800 A | 5/1997 | Blank et al. |
| 2004/0024367 A1 * | 2/2004 | Gilbert .................. A61M 5/326 604/198 |

(Continued)

FOREIGN PATENT DOCUMENTS

| CA | 2215912 | 5/2007 |
| CN | 102481417 | 5/2012 |

(Continued)

OTHER PUBLICATIONS

International Preliminary Report on Patentability in International Application No. PCT/EP2017/076056, dated May 7, 2019, 7 pages.

(Continued)

*Primary Examiner* — Bradley J Osinski
(74) *Attorney, Agent, or Firm* — Fish & Richardson P.C.

(57) ABSTRACT

A feedback mechanism for an injection device that is configured to deliver a medicament to a user is described. The feedback mechanism comprises a piston and a fluid chamber, and the piston is adapted to move into the fluid chamber during use of the injection device. The feedback mechanism also has a damper that is arranged to damp movement of the piston, and an indicator that is arranged to provide feedback to the user after the piston has moved a pre-determined distance into the fluid chamber.

8 Claims, 11 Drawing Sheets

(51) Int. Cl.
*A61M 5/20* (2006.01)
*A61M 5/24* (2006.01)

(52) U.S. Cl.
CPC ... *A61M 5/2459* (2013.01); *A61M 2005/2086* (2013.01); *A61M 2205/581* (2013.01)

(56) References Cited

U.S. PATENT DOCUMENTS

| | | | |
|---|---|---|---|
| 2008/0114304 A1 | 5/2008 | Nalesso et al. | |
| 2011/0071477 A1* | 3/2011 | Guillermo | A61M 11/007 604/225 |
| 2013/0090605 A1 | 4/2013 | O'Connor et al. | |
| 2013/0218093 A1* | 8/2013 | Markussen | A61M 5/2033 604/198 |
| 2014/0276898 A1 | 9/2014 | Novak | |
| 2015/0165129 A1 | 6/2015 | Row et al. | |
| 2015/0209517 A1* | 7/2015 | Brunnberg | A61M 5/3157 604/198 |
| 2017/0182253 A1* | 6/2017 | Folk | F16F 9/361 |

FOREIGN PATENT DOCUMENTS

| | | |
|---|---|---|
| CN | 103118723 | 5/2013 |
| CN | 103379933 | 10/2013 |
| CN | 104080499 | 10/2014 |
| CN | 105263545 | 1/2016 |
| CN | 105358195 | 2/2016 |
| CN | 105722539 | 6/2016 |
| CN | 105792866 | 7/2016 |
| EP | 0652019 | 5/1995 |
| EP | 1693078 | 8/2006 |
| JP | 2011-520540 | 7/2011 |
| JP | 2013-536032 | 9/2013 |
| JP | 2017-518791 | 7/2017 |
| JP | 2017-528217 | 9/2017 |
| WO | WO 2009/141219 | 11/2009 |
| WO | WO 2011/006086 | 1/2011 |
| WO | WO 2012/022810 | 2/2012 |
| WO | WO 2012/025639 | 3/2012 |
| WO | WO 2012/094403 | 7/2012 |
| WO | WO 2012/140097 | 10/2012 |
| WO | WO 2013/057033 | 4/2013 |
| WO | WO 2014/026935 | 2/2014 |
| WO | WO 2014/191190 | 12/2014 |
| WO | WO 2014/195183 | 12/2014 |
| WO | WO 2015/004047 | 1/2015 |
| WO | WO 2015/073740 | 5/2015 |
| WO | WO 2015/084428 | 6/2015 |
| WO | WO 2015/166286 | 11/2015 |
| WO | WO 2015/171777 | 11/2015 |
| WO | WO 2016/034407 | 3/2016 |

OTHER PUBLICATIONS

International Search Report and Written Opinion in International Application No. PCT/EP2017/076056, dated Januaty 19, 2018, 11 pages.

* cited by examiner

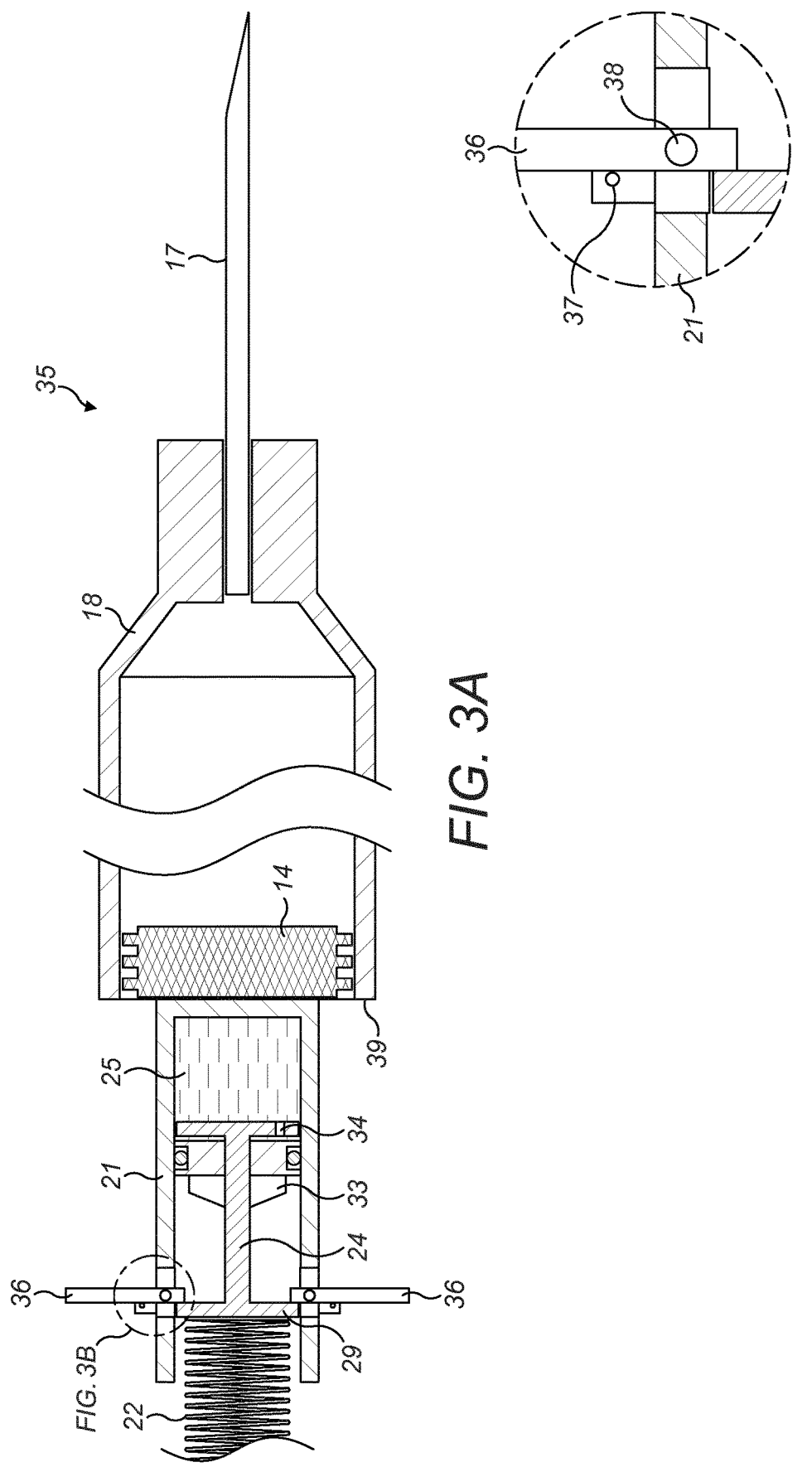

FEEDBACK MECHANISM FOR AN INJECTION DEVICE

CROSS REFERENCE TO RELATED APPLICATIONS

The present application is the national stage entry of International Patent Application No. PCT/EP2017/076056, filed on Oct. 12, 2017, and claims priority to Application No. EP 16196676.7, filed on Nov. 1, 2016, the disclosures of which are incorporated herein by reference.

TECHNICAL FIELD

The present disclosure relates to a feedback mechanism for an injection device.

BACKGROUND

Injection devices, such as auto-injectors, typically have a syringe into which a plunger is pushed to dispense medicament from the syringe into the patient via a needle. The injection process is completed when the plunger has been pushed the appropriate distance into the syringe. It is known to provide a feedback mechanism for indicating to the user when the appropriate volume of medicament has been injected.

SUMMARY

It is an object of the present disclosure to provide a feedback mechanism for an injection device that provides feedback to a user.

According to a first aspect, there is provided a feedback mechanism for an injection device, said injection device being configured to deliver a medicament to a user, the feedback mechanism comprising:
  a piston and a fluid chamber, the piston being adapted to move into the fluid chamber during use of the injection device;
  a damper arranged to damp movement of the piston; and,
  an indicator arranged to provide feedback to said user after the piston has moved a pre-determined distance into the fluid chamber.

The feedback mechanism may further comprise a biasing member arranged to urge the piston into the fluid chamber during use.

The damper may comprise a rotary agitator disposed within the fluid chamber, and wherein movement of the piston into the fluid chamber may cause rotation of the rotary agitator such that the movement of the piston is damped by the rotary agitator.

The piston may comprise the rotatory agitator.

The piston may comprise a plate that extends across the fluid chamber, and the damper may comprise one or more orifices located in the plate through which fluid flows as the piston moves into the fluid chamber.

The feedback mechanism may further comprise a recipient chamber into which fluid is urged as the piston moves into the fluid chamber, and wherein the damper may comprise an orifice arranged between the fluid chamber and the recipient chamber.

The recipient chamber may comprise a slider that is moved by fluid passing into the recipient chamber, and wherein the slider may be configured to engage the indicator after the slider has moved a predetermined distance, and wherein the indicator may provide feedback to said user after being engaged.

The indicator may be disposed between the piston and a part of said injection device, such that movement of the piston into the fluid chamber causes the indicator to be engaged by the piston and/or said part of said injection device, and wherein the indicator may provide feedback to said user after being engaged.

The indicator may comprise a sound generator that generates an audible sound.

The sound generator may comprise a pre-stressed element that generates an audible sound when deflected.

According to a further aspect, there is also provided an injection device comprising a medicament delivery mechanism comprising a reservoir and a plunger that moves to displace medicament from the reservoir for delivery to a user during use of the injection device; and, the feedback mechanism described above.

The injection device may further comprise a biasing member arranged to push the plunger into the reservoir during use.

The biasing member may be arranged to act on the piston, and wherein the piston and plunger may be arranged such that force applied to the piston is transferred to the plunger via the fluid chamber.

The damper may comprise an orifice formed in the plunger.

The injection device may further comprise a housing, and wherein the damper may comprise an orifice formed in the housing.

The indicator may comprise a pre-stressed element that generates an audible sound when deflected, the pre-stressed element being mounted to the plunger and arranged to be deflected as the plunger moves to displace medicament.

The plunger may comprise an arm to which the pre-stressed element is mounted, the arm being arranged to engage a feature of the piston as the piston moves into the fluid chamber, and wherein the arm is arranged to deflect the pre-stressed element after engaging with the feature of the piston.

The injection device may be configured such that the piston begins moving into the fluid chamber after the plunger has moved a pre-determined distance into the reservoir.

The injection device may further comprise a locking mechanism arranged to hold the piston until the plunger has reached a pre-determined position, and to then release the piston such that the piston can move into the fluid chamber.

The reservoir may contain a medicament.

According to a further aspect, there is also provided a method of using an injection device, the method comprising:
  delivering a medicament to a user;
  moving a piston into a fluid chamber;
  damping said movement of the piston; and,
  providing feedback to said user after the piston has moved a pre-determined distance into the fluid chamber.

These and other aspects will be apparent from and elucidated with reference to the embodiments described hereinafter.

BRIEF DESCRIPTION OF THE FIGURES

Embodiments will now be described, by way of example only, with reference to the accompanying drawings, in which:

FIG. 3A is a cross-sectional side view of an injection device having a damper, an indicator and a locking mechanism, shown before the injection device has been used;

FIG. 3B is a magnified cross-sectional side view of the locking mechanism of the injection device of FIG. 3A;

DETAILED DESCRIPTION

Figure 1A:
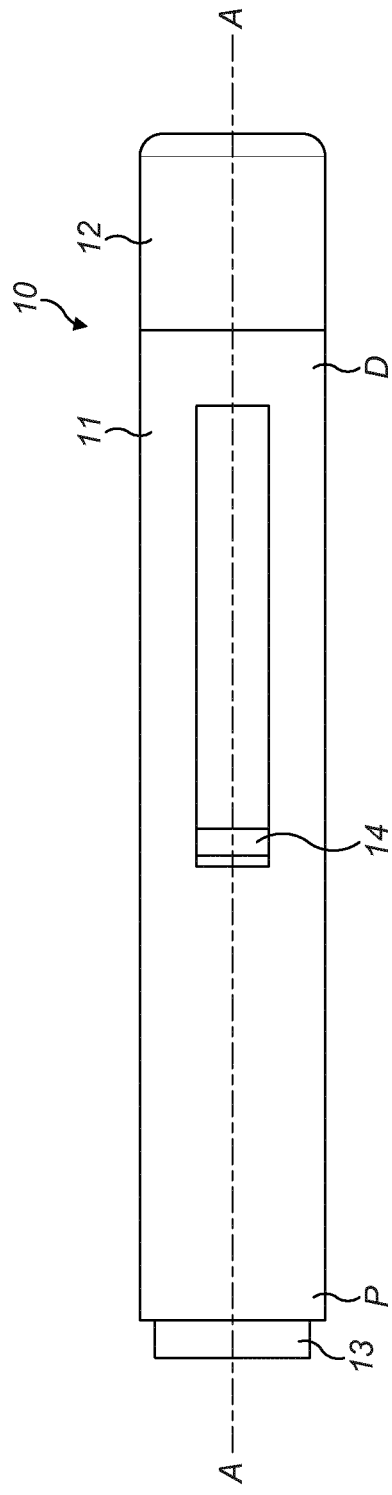
FIG. 1A is a schematic side view of an injection device and a removable cap.

A drug delivery device, as described herein, may be configured to inject a medicament into a patient. For example, delivery could be sub-cutaneous, intra-muscular, or intravenous. The user of such a device could be a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 17 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include an actuator, for example, one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Figure 1B:
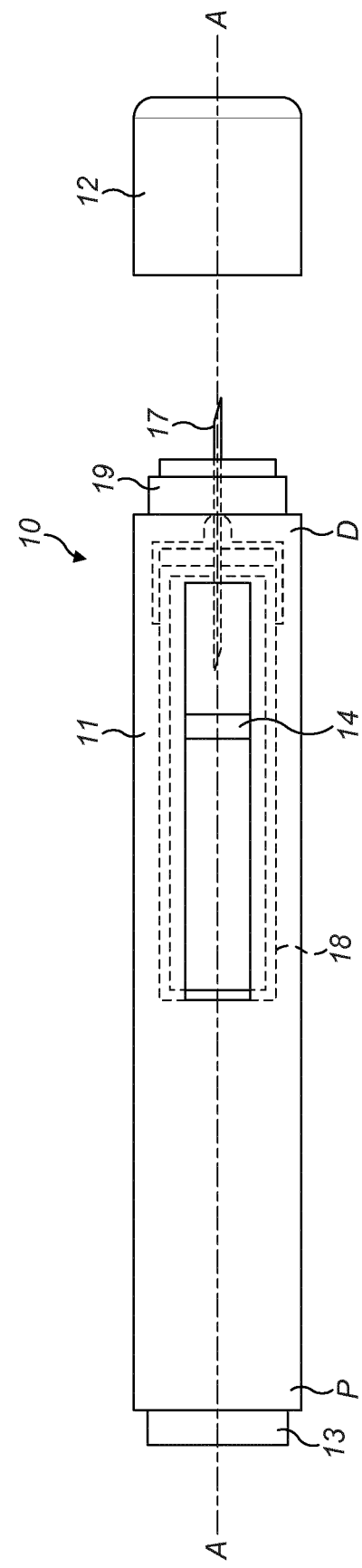
FIG. 1B is a schematic side view of the injection device of FIG. 1A, with the cap removed from the housing.

According to some embodiments of the present disclosure, an exemplary drug delivery device 10 is shown in FIGS. 1A & 1B. Device 10, as described above, is configured to inject a medicament into a patient's body. Device 10 includes a housing 11 which typically contains a syringe 18 containing the medicament to be injected and the components required to facilitate one or more steps of the delivery process. A cap 12 is also provided that can be detachably mounted to the housing 11. Typically, a user must remove cap 12 from housing 11 before device 10 can be operated.

As shown, housing 11 is substantially cylindrical and has a substantially constant diameter along the longitudinal axis A-A. The housing 11 has a distal region D and a proximal region P. The term "distal" refers to a location that is relatively closer to a site of injection, and the term "proximal" refers to a location that is relatively further away from the injection site.

Device 10 can also include a needle sleeve 19 coupled to housing 11 to permit movement of sleeve 19 relative to housing 11. For example, sleeve 19 can move in a longitudinal direction parallel to longitudinal axis A-A. Specifically, movement of sleeve 19 in a proximal direction can permit a needle 17 to extend from distal region D of housing 11.

Insertion of needle 17 can occur via several mechanisms. For example, needle 17 may be fixedly located relative to housing 11 and initially be located within an extended needle sleeve 19. Proximal movement of sleeve 19 by placing a distal end of sleeve 19 against a patient's body and moving housing 11 in a distal direction will uncover the distal end of needle 17. Such relative movement allows the distal end of needle 17 to extend into the patient's body. Such insertion is termed "manual" insertion as needle 17 is manually inserted via the patient's manual movement of housing 11 relative to sleeve 19.

Another form of insertion is "automated", whereby needle 17 moves relative to housing 11. Such insertion can be triggered by movement of sleeve 19 or by another form of activation, such as, for example, a button 13. As shown in FIGS. 1A & 1B, button 13 is located at a proximal end of housing 11. However, in other embodiments, button 13 could be located on a side of housing 11.

Other manual or automated features can include drug injection or needle retraction, or both. Injection is the process by which a bung 14 is moved from a proximal location within a syringe 18 to a more distal location within the syringe 18 in order to force a medicament from the syringe 18 through needle 17. In some embodiments, a drive spring (not shown) is under compression before device 10 is activated. A proximal end of the drive spring can be fixed within proximal region P of housing 11, and a distal end of the drive spring can be configured to apply a compressive force to a proximal surface of bung 14. Following activation, at least part of the energy stored in the drive spring can be applied to the proximal surface of bung 14. This compressive force can act on bung 14 to move it in a distal direction. Such distal movement acts to compress the liquid medicament within the syringe 18, forcing it out of needle 17.

Following injection, needle 17 can be retracted within sleeve 19 or housing 11. Retraction can occur when sleeve 19 moves distally as a user removes device 10 from a patient's body. This can occur as needle 17 remains fixedly located relative to housing 11. Once a distal end of sleeve 19 has moved past a distal end of needle 17, and needle 17 is covered, sleeve 19 can be locked. Such locking can include locking any proximal movement of sleeve 19 relative to housing 11.

Another form of needle retraction can occur if needle 17 is moved relative to housing 11. Such movement can occur if the syringe 18 within housing 11 is moved in a proximal direction relative to housing 11. This proximal movement can be achieved by using a retraction spring (not shown), located in distal region D. A compressed retraction spring, when activated, can supply sufficient force to the syringe 18 to move it in a proximal direction. Following sufficient retraction, any relative movement between needle 17 and housing 11 can be locked with a locking mechanism. In addition, button 13 or other components of device 10 can be locked as required.

Figure 2A:
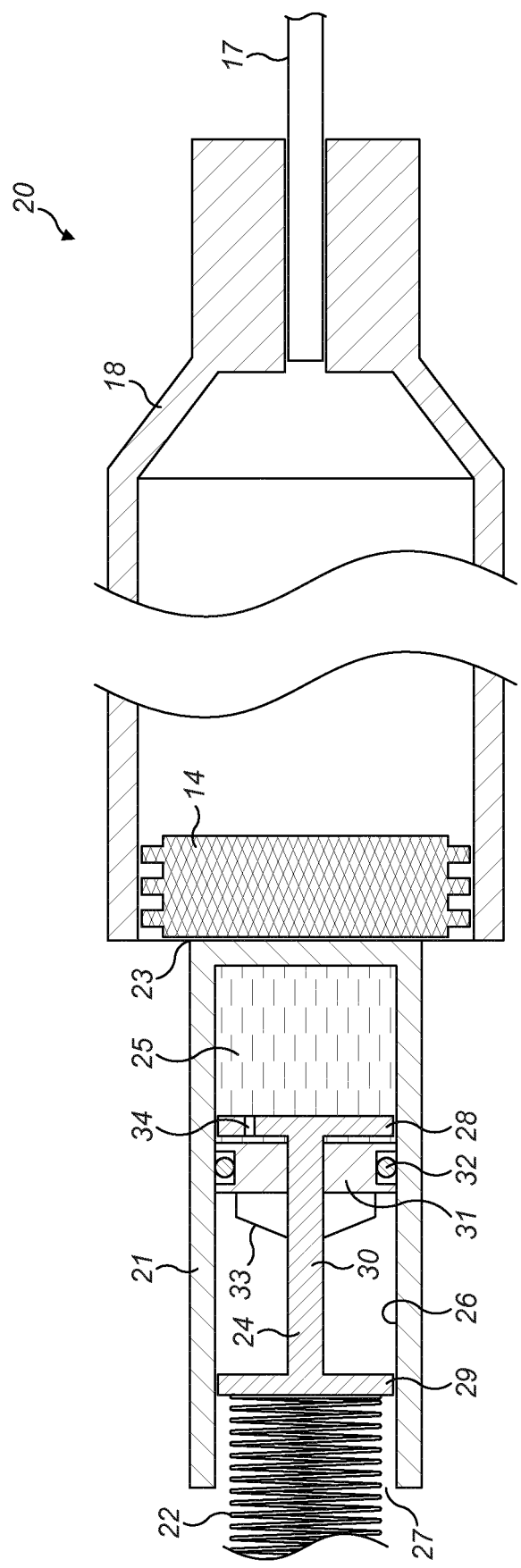
FIG. 2A is a cross-sectional side view of an injection device having a damper and an indicator, shown before the injection device has been used.
Figure 2B:
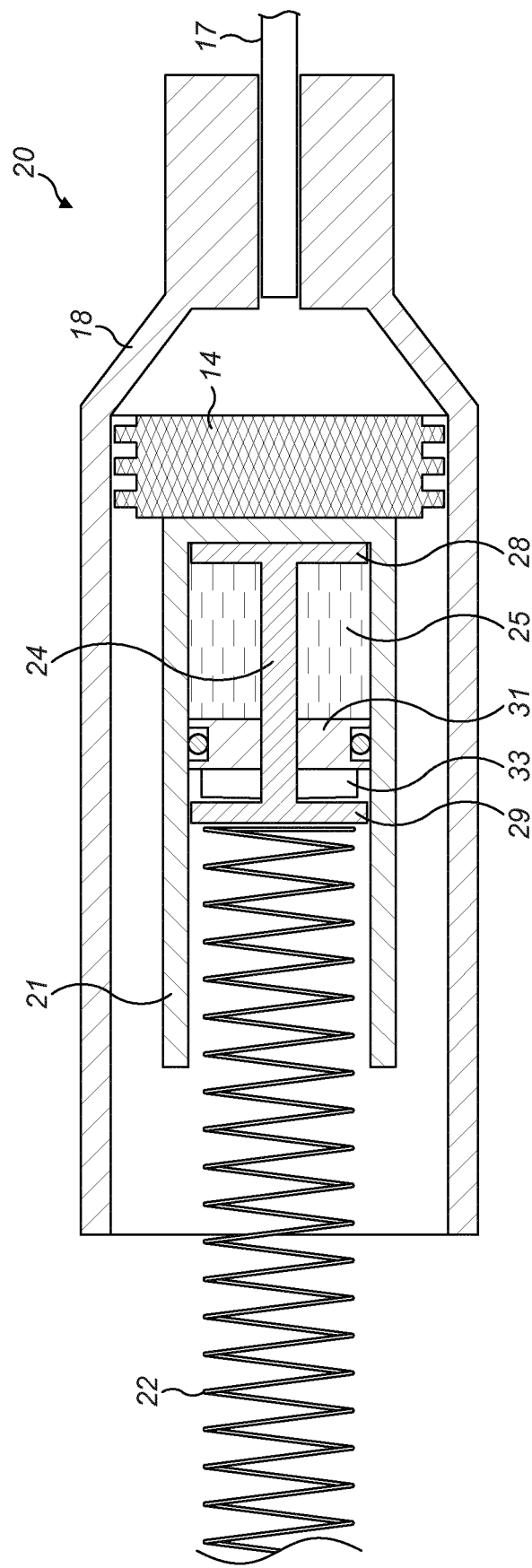
FIG. 2B is a cross-sectional side view of the injection device of FIG. 2A, after the injection device has been used.

FIG. 2A and FIG. 2B show an example injection device 20 that includes a syringe 18, similar to as described above with reference to FIG. 1A and FIG. 1B. The injection device 20 of FIG. 2A also includes a housing (not shown).

As illustrated, the injection device 20 also includes a plunger 21 that acts on the bung 14 to move the bung 14 into the syringe 18 and dispense medicament through the needle 17. A drive spring 22 is provided to push the plunger 21 against the bung 14 and into the syringe 18 during use of the injection device 20. The drive spring 22 may be pre-loaded, and a release mechanism may be provided to release the plunger 21 such that the drive spring 22 can push the plunger 21 and bung 14 to dispense medicament, as described previously. It will be appreciated that the bung 14 may be omitted and the end 23 of the plunger 21 may act as a bung within the syringe 18.

The injection device 20 of FIG. 2A also includes a delay mechanism that provides delayed user feedback at a time after the plunger 21 has moved into the syringe 18. This delayed feedback informs the user that the medicament has been dispensed, and the delay provides time for the medicament to have dispersed from the injection site.

As illustrated, the injection device 20 of this example includes a damper, in this example a piston 24 and fluid chamber 25 that are located within the plunger 21. The plunger 21 is elongate and has a cylindrical bore 26 with an opening 27 at the distal end of the plunger 21, in which the piston 24 and fluid chamber 25 are located.

As shown, the piston 24 of this example is formed of a disc 28 and an opposite end 29, and a web 30 connecting the disc 28 and the opposite end 29. The web 30 provides free space in the area surrounding the web 30 between the disc 28 and the opposite end 29. Also provided is a sealing plate 31 fixed in the cylindrical bore 26, including a seal 32. The sealing plate 31 includes an aperture through which the web 30 of the piston 24 extends, such that the disc 28 is on a first (proximal) side of the sealing plate 31 and the opposite end 29 is on a second (distal) side of the sealing plate 31. The fluid chamber 25 is defined between the sealing plate 31 and the end of the cylindrical bore 26 within the plunger 21.

In this way, the disc 28 is located within the fluid chamber 25. The drive spring 22 acts between the opposite end 29 of the piston 24 and the housing (not shown) of the injection device 20. The drive spring 22 pushes the piston 24 towards the fluid chamber 25.

An indicator, in this example a sound generator 33, is located between the sealing plate 31 and the opposite end 29 of the piston 24. In this example, the sound generator 33 is fixed to the proximal side of the sealing plate 31, but it may alternatively be fixed to the piston 24. The sound generator 33 comprises a pre-stressed member that generates a sound when deflected (as explained below), which provides the user with an audible indication.

During use of the injection device 20 the drive spring 22 pushes the piston 24, which in turn applies a compressive force to the fluid chamber 25, which in turn urges the plunger 21 against the bung 14 and into the syringe 18. That is, the force of the drive spring 22 is provided to the plunger 21 via the piston 24 and fluid chamber 25.

The disc 28 of the piston 24 is provided with at least one orifice 34 through which the fluid in the fluid chamber 25 passes as the piston 24 is urged in a proximal direction by the drive spring 22. The orifice(s) 34 allows fluid to pass through the disc 28, from a proximal side to a distal side, and therefore allows the piston 24 to move proximally. As the piston 24 moves proximally, the web 30 slides within the aperture of the sealing plate 31 and fluid gradually moves into the space between the sealing plate 31 and the disc 28 of the piston 24.

The orifice(s) 34 is of restricted size to limit the rate at which fluid can pass through the orifice(s) 34 as the drive spring 22 pushes against the piston 24. The orifice(s) 34 thereby form a damper that damps movement of the piston 24 into the fluid chamber 25.

The rate at which the piston 24 is able to move in a proximal direction depends on the rate at which the fluid can pass through the orifice(s) 34, which is dependent on the viscosity of the fluid and the size and number of the orifice(s) 34, as well as the force applied by the drive spring 22.

As illustrated in FIG. 2B, when the piston 24 has moved completely or almost completely into the fluid chamber 25 the sound generator 33 is deflected by the opposite end 29 and/or the sealing plate 31. Deflection of the sound generator 33 creates an audible sound that provides the user with an indication.

In this example, the rate of fluid movement through the orifice(s) 34 is configured such that the piston 24 reaches the point at which the sound generator 33 is deflected at a time after the plunger 21 has reached the end of its movement into the syringe 18. In particular, for the given force of the drive spring 22 the time taken for the bung 14 to be pushed into the syringe 18 is less than the time taken for the piston 24 to be pushed into the fluid chamber 25 and the sound generator 33 to be deflected.

Therefore, the user is provided with the indication at a time after the medicament has been dispensed from the syringe 18. This delayed feedback provides for dispersion of the medicament from the injection site.

The duration of the delay may be, for example, more than 2 seconds, or more than 5 seconds, or more than 10 seconds, or between 10 and 30 seconds, or between 10 and 20 seconds.

FIG. 3A and FIG. 3B show an example injection device 35 that is similar to that described with reference to FIG. 2A and FIG. 2B. In this example, the injection device 35 also has a locking mechanism that holds the piston 24 in a locked position until the plunger 21 and bung 14 have been moved a pre-determined distance into the syringe 18.

The locking mechanism includes locking arms 36 that are pivotally attached to the plunger 21 at pivots 38 and engage a distal side of the opposite end 29 of the piston 24, as shown in FIG. 3A and FIG. 3B. A stop 37 is provided for each locking arm 36, the stops 37 being located on the plunger 21 and the stops 37 are arranged to prevent rotation of the locking arms 36 as the plunger 21 and bung 14 are moved into the syringe 18.

In particular, as the drive spring 22 acts on the piston 24 force is transferred to the plunger 21 via the locking arms 36 and stops 37, rather than via the disc 28 and fluid chamber 25. Therefore, the locking arms 36 remain in the position illustrated in FIG. 3A and FIG. 3B while the plunger 21 and bung 14 move into the syringe 18 to dispense medicament.

At or towards the end of the movement of the plunger 21 into the syringe 18 the locking arms 36 abut against the annular end 39 of the syringe 18. The leverage caused by the locking arms 36 abutting against the annular end 39 of the syringe 18 causes the locking arms 36 to either break or deform the stops 37, allowing the locking arms 36 to rotate and release the engagement between the piston 24 and plunger 21. Thereafter, the force of the drive spring 22 acts to push the piston 24 into the fluid chamber 25, eventually triggering the sound generator 33 after a delay caused by the damper (orifice(s) 34), as described with reference to FIG. 2A and FIG. 2B.

The locking mechanism thereby prevents movement of the piston 24 until the plunger 21 has dispensed all or most of the medicament through the needle 17. This is advantageous as it removes the variations in time for the fluid to pass through the orifice(s) 34 in the disc 28, which may be caused by temperature and back pressure differences.

In an alternative example, the locking arms 36 may not be pivotally mounted, but may themselves be broken or deformed when they contact the annular end 39 of the syringe 18, thereby allowing the piston 24 to move independently of the plunger 21.

Figure 4:
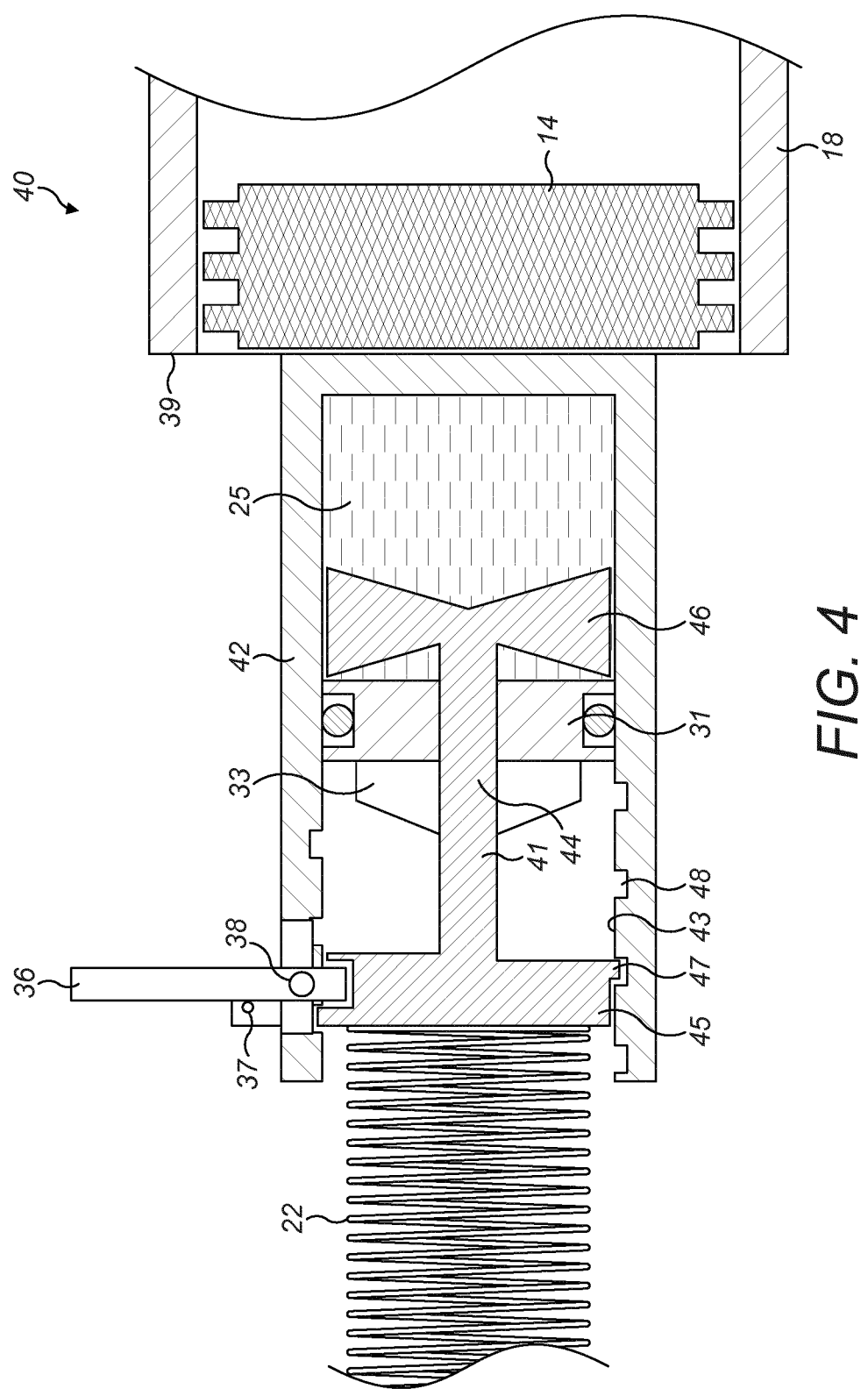
FIG. 4 is a cross-sectional side view of another injection device having a damper and an indicator, shown before the injection device has been used.

FIG. 4 shows an alternative example injection device 40 that includes a syringe 18 and a bung 14, similar to as described above with reference to FIG. 2A, FIG. 2B, and FIG. 3.

The injection device 40 of this example also comprises a drive spring 22 that acts on a piston 41 which in turn acts on a plunger 42 to drive the plunger 42 into the syringe 18. A locking mechanism locks in the piston 41 to the plunger 42 until the plunger 42 has moved into the syringe 18, in the same way as described above with reference to FIG. 3. In particular, locking arms 36 are pivotally attached to the plunger 42 at pivots 38 and engage with the piston 41 until they contact the annular end 39 of the syringe 18. At this point, the stops 37 are broken and the locking arms 36 can rotate and release the piston 41 from the plunger 42. Thereafter, the drive spring 22 acts to push the piston 41 into a fluid chamber 25 formed within a cylindrical bore 43 of the plunger 42 and closed by a sealing plate 31.

The sealing plate 31 is located in the plunger 42 and the piston 41 includes a web 44 that passes through an aperture in the sealing plate 31, similarly to the example of FIG. 3A and FIG. 3B. The drive spring 22 abuts against a proximal end 45 of the piston 41, and a sound generator 33, in this example a pre-stressed member, is located between the proximal end 45 and the sealing plate 31. The distal end of the piston 41, located in the fluid reservoir 25, includes a damper in the form of a rotary agitator 46.

The rotary agitator 46 comprises one or more fins, paddles, or angled plates that create resistance as the rotary agitator 46 rotates within the fluid in the fluid chamber 25.

The proximal end 45 of the piston 41 includes at least one protrusion 47 that engages with a thread 48 formed in the cylindrical bore 43 of the plunger 42. The thread 48 is helical along the cylindrical bore 43, and so to move axially within the injection device 40 the piston 41 must rotate so that the protrusion(s) 47 move along the thread 48.

Therefore, after the locking arms 36 have released the piston 41 from the plunger 42, and the drive spring 22 is pushing the piston 41 in a distal direction, the piston 41 rotates within the plunger 42. This rotation is damped by the rotation of the rotary agitator 46 within the fluid chamber 25. This resistance delays the progress of the piston 41 in a distal direction.

Once the piston 41 has been pushed/rotated towards the end of the fluid chamber 25 the sound generator 33 is compressed between the proximal end 45 of the piston 41 and the sealing plate 31, and is deflected. The sound generator generates an audible sound as it is deflected, providing the user with an audible indication.

The duration of the delay between the start of the movement of the piston 41 and the compression of the sound generator 33 may be, for example, more than 2 seconds, or more than 5 seconds, or more than 10 seconds, or between 10 and 30 seconds, or between 10 and 20 seconds.

In this example, the piston 41 only starts moving into the fluid chamber 25 after the bung 14 is at or near the end of the syringe 18, and so the indication is provided to the user at a time after the medicament has been injected. This allows time for the medicament to disperse from the injection site.

In an alternative example, the locking mechanism (locking arms) are omitted, and the damping provided by the rotary agitator 46 and fluid chamber 25 is increased such that, for a given force from the drive spring 22, the time taken for the piston 41 to move from the initial position to the position in which the sound generator 33 is triggered is greater than the time required to move the bung 14 to the end of the syringe 18 and dispense all of the medicament. In this way, the audible indication is provided at a time after the medicament has been dispensed, allowing for dispersal of the medicament from the injection site.

Figure 5A:
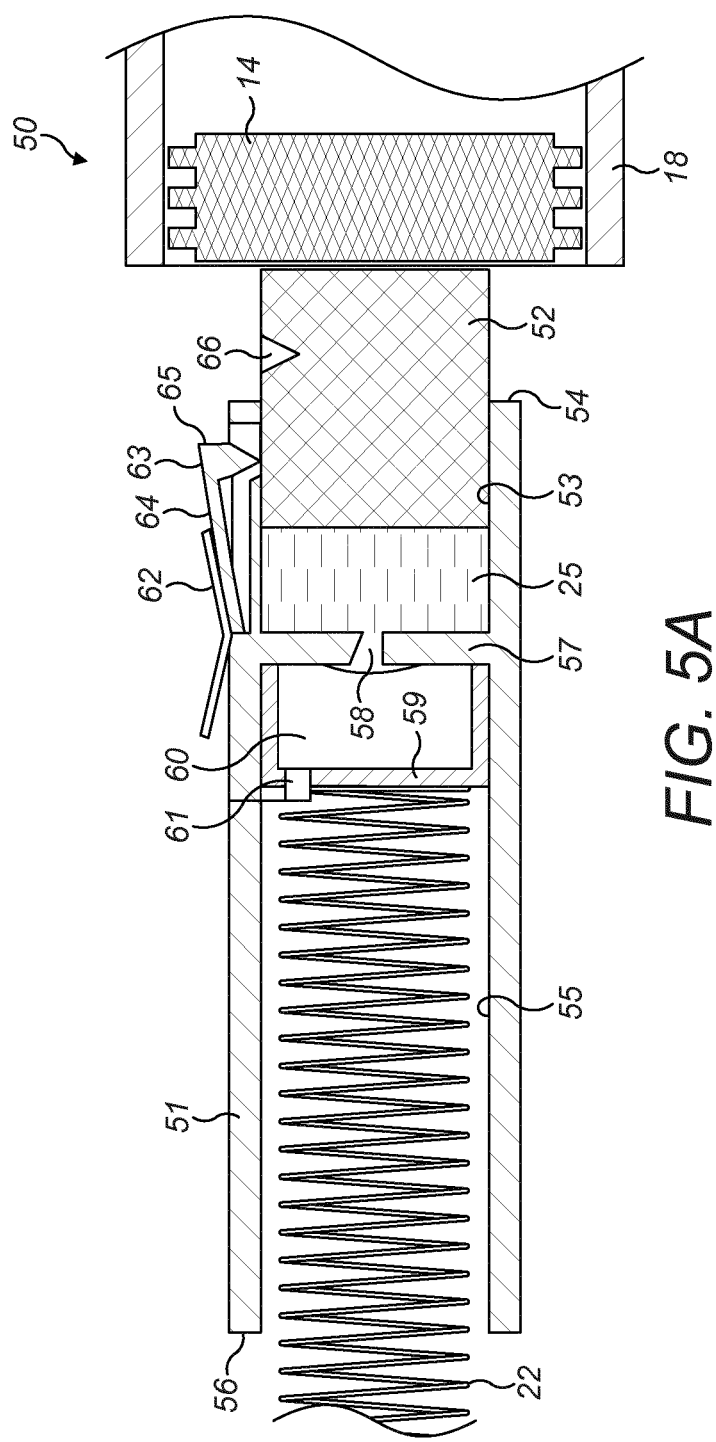
FIG. 5A is a cross-sectional side view of another injection device having a damper and an indicator, shown before the injection device has been used.

FIG. 5A shows an alternative example injection device 50 that includes a bung 14 and syringe 18, similar to as described previously. In particular, the injection device 50 has a syringe 18 and a bung 14 that is pushed into the syringe 18 by a plunger 51. In this example, a piston 52 is located between the plunger 51 and the bung 14, and the piston 52 is received in a recess 53 in the distal end 54 of the plunger 51. A fluid chamber 25 is defined in the recess 53 and the piston 52 seals the fluid chamber 25. The drive spring 22 urges the plunger 51 against the piston 52, which in turn is urged against the bung 14.

The plunger 51 includes a cylindrical bore 55 extending from the proximal end 56 of the plunger 51, and the recess 53 is located in the distal end 54 of the plunger 51. A wall 57 separates the cylindrical bore 55 and the recess 53 and the wall 57 includes at least one orifice 58 through which fluid passes as the piston 52 moves into the recess 53 to compress the fluid chamber 25.

The fluid in the fluid chamber 25 and orifice 58 create a damper that damps movement of the piston 52 into the fluid chamber 25.

On the proximal side of the wall 57 (opposite to the fluid chamber 25) is a spacer 59 that defines a recipient chamber 60 that is in fluid communication with the orifice 58, such that fluid passing from the fluid chamber 25 through the orifice 58 passes into the recipient chamber 60. The recipient chamber 60 includes an air outlet 61 so that the air displaced by the fluid can escape.

The drive spring 22 pushes on the spacer 59 and in turn the wall 57, and so drives the plunger 51 towards the bung 14 and piston 52. In so doing the piston 52 is moved into the fluid chamber 25 and fluid is forced through the orifice 58 into the recipient chamber 60. The rate of movement of fluid through the orifice 58 determines the rate at which the piston 52 moves into the recess 53. Therefore, by defining the fluid viscosity and size and number of orifices 58, the rate at which the piston 52 moves into the recess 53 can be defined.

The injection device 50 of this example also includes an indicator, in this example a sound generator. As illustrated, the sound generator includes a pre-stressed member 62 that is located on the plunger 51 and moves with the plunger 51 as the plunger 51 moves towards the syringe 18.

As illustrated, the plunger 51 also includes a clip 63 that holds the pre-stressed member 62 in a first state as the plunger 51 moves into the syringe 18. The clip includes an arm 64 and a head 65, and the head 65 is in contact with, and urged against, the side of the piston 52. The head 65 may be urged against the side of the piston 52 by a biasing member (not shown) or by the force provided by the pre-stressed member 62.

Figure 5B:
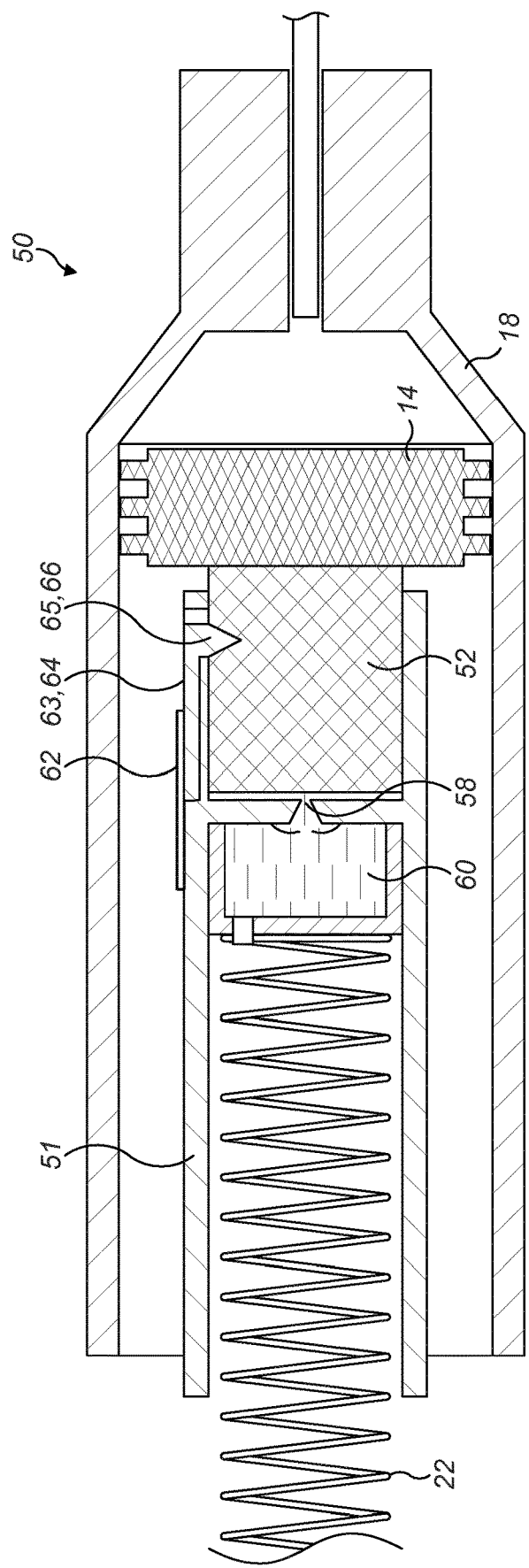
FIG. 5B is a cross-sectional side view of the injection device of FIG. 5A, after the injection device has been used.

The piston 52 includes a notch 66 adapted to receive the head 65 of the clip 63 once the piston 52 has moved a pre-determined distance into the fluid chamber 25. As illustrated in FIG. 5A, in an initial position the head 65 of the clip 63 is located proximally of the notch 66, and as the drive spring 22 causes the piston 52 to move into the fluid chamber 25 the head 65 and notch 66 come into alignment, as shown in FIG. 5B. Once aligned, the arm 64 deflects inwards and the pre-stressed member 62 is deflected, generating an audible sound that provides an indication to the user.

The viscosity of the fluid and the size and number of orifices 58 are selected such that the drive spring 22 pushes the bung 14 completely into the syringe 18, to dispense all of the medicament, before the piston 52 reaches the point at which the audible indication is generated. In this way, the feedback is provided at a time after the medicament has been injected, allowing for the medicament to disperse from the injection site.

The arrangement of the damper creates a delay between the start of the movement of the piston 52 into the fluid chamber 25, and the time at which the sound generator 62 generates a sound. The duration of the delay may be, for example, more than 2 seconds, or more than 5 seconds, or more than 10 seconds, or between 10 and 30 seconds, or between 10 and 20 seconds.

Figure 6A:
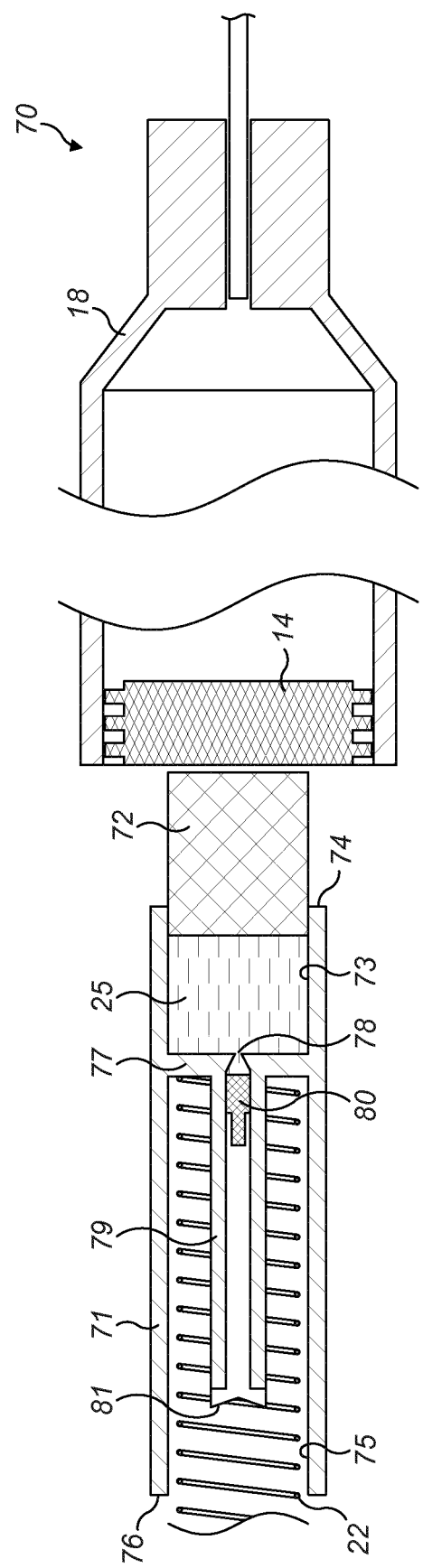
FIG. 6A is a cross-sectional side view of another injection device having a damper and an indicator, shown before the injection device has been used.

FIG. 6A shows an alternative example injection device 70 similar to the example described with reference to FIG. 5. In particular, the injection device 70 has a syringe 18 and a bung 14 that is pushed into the syringe 18 by a plunger 71. A piston 72 is located between the plunger 71 and the bung 14, and the piston 72 is received in a recess 73 in the distal end 74 of the plunger 71. The recess 73 forms a fluid chamber 25 and the piston 72 seals the fluid chamber 25.

The plunger 71 includes a cylindrical bore 75 extending from the proximal end 76 of the plunger 71, and the recess 73 is located in the distal end 74 of the plunger 71. A wall 77 separates the cylindrical bore 75 and the recess 73, and the wall 77 includes an orifice 78 through which fluid passes as the piston 72 moves into the fluid chamber 25.

An elongate recipient chamber 79 is formed on the proximal side of the wall 79 (opposite to the fluid chamber 25), such that fluid passing from the fluid chamber 25 through the orifice 78 passes into the recipient chamber 79. A slider 80 is located within the elongate recipient chamber 79 and the slider 80 is initially in a distal position, proximate to the wall 77.

The drive spring 22 pushes on the wall 77 and so drives the plunger 71 towards the bung 14 and syringe 18. In so doing the piston 72 is moved into the fluid chamber 25 and fluid is forced through the orifice 78 into the elongate recipient chamber 79. The rate of movement through the orifice 78 defines the rate at which the piston 72 moves into the fluid chamber 25. Therefore, by defining the fluid viscosity and size and number of orifices 78, the rate at which the piston 72 moves into the fluid chamber 25 can be defined.

The injection device 70 of this example also includes an indicator, in this example a sound generator. As illustrated, the sound generator includes a pre-stressed member 81 that is located at the proximal end of the elongate recipient chamber 79, opposite to the orifice 78. The pre-stressed member 81 is initially in deflected state, as shown in FIG. 6A.

Figure 6B:
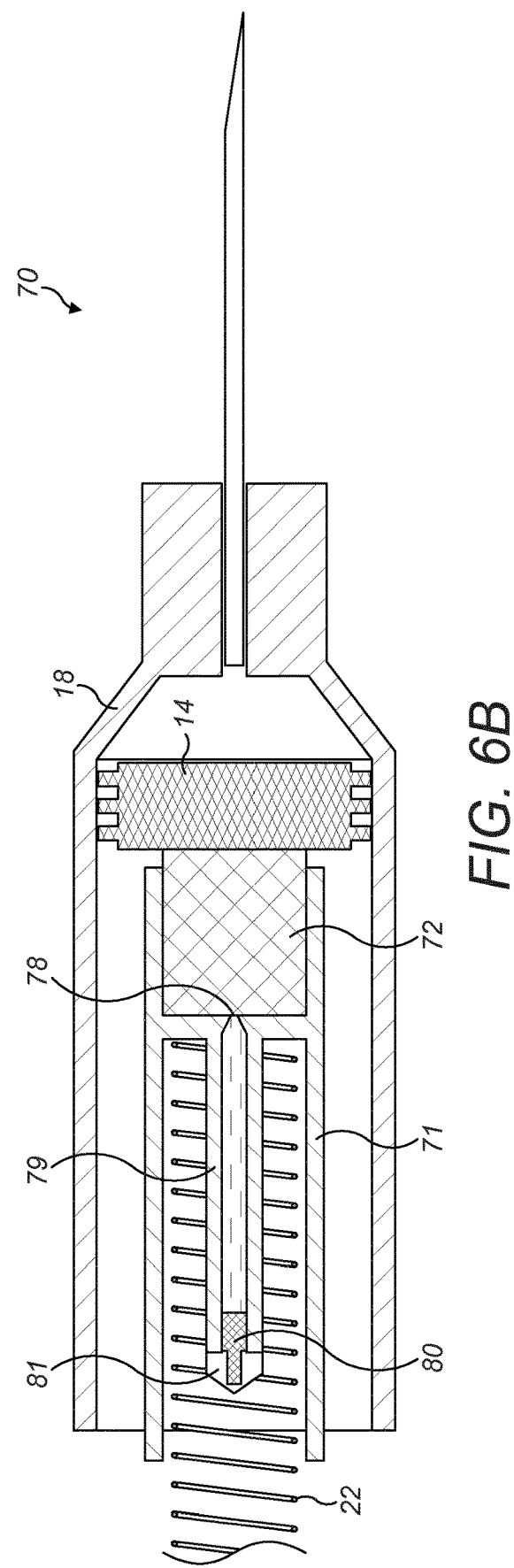
FIG. 6B is a cross-sectional side view of the injection device of FIG. 6A, after the injection device has been used.

As the drive spring 22 pushes the plunger 71 against the piston 72 and bung 14 the piston 72 gradually moves into the fluid chamber 25 and fluid is pushed through the orifice 78 into the elongate recipient chamber 79. As fluid passes into the elongate recipient chamber 79 it pushes the slider 80 in a proximal direction, towards the pre-stressed member 81. Eventually, as shown in FIG. 6B, the slider 80 contacts the pre-stressed member 81 and deflects the pre-stressed member 81, generating an audible sound which provides an indication to the user.

The viscosity of the fluid and the size of the orifice 78 can be selected such that the drive spring 22 pushes the bung 14 completely into the syringe 18, to dispense all of the medicament, before the slider 80 reaches the pre-stressed element 81. In this way, there is a delay between time at which the medicament has been completely dispensed and the time at which the sound generator 81 is contacted by the slider 80, allowing time for the medicament to disperse from the injection site.

The duration of the delay may be, for example, more than 2 seconds, or more than 5 seconds, or more than 10 seconds, or between 10 and 30 seconds, or between 10 and 20 seconds.

Figure 7A:
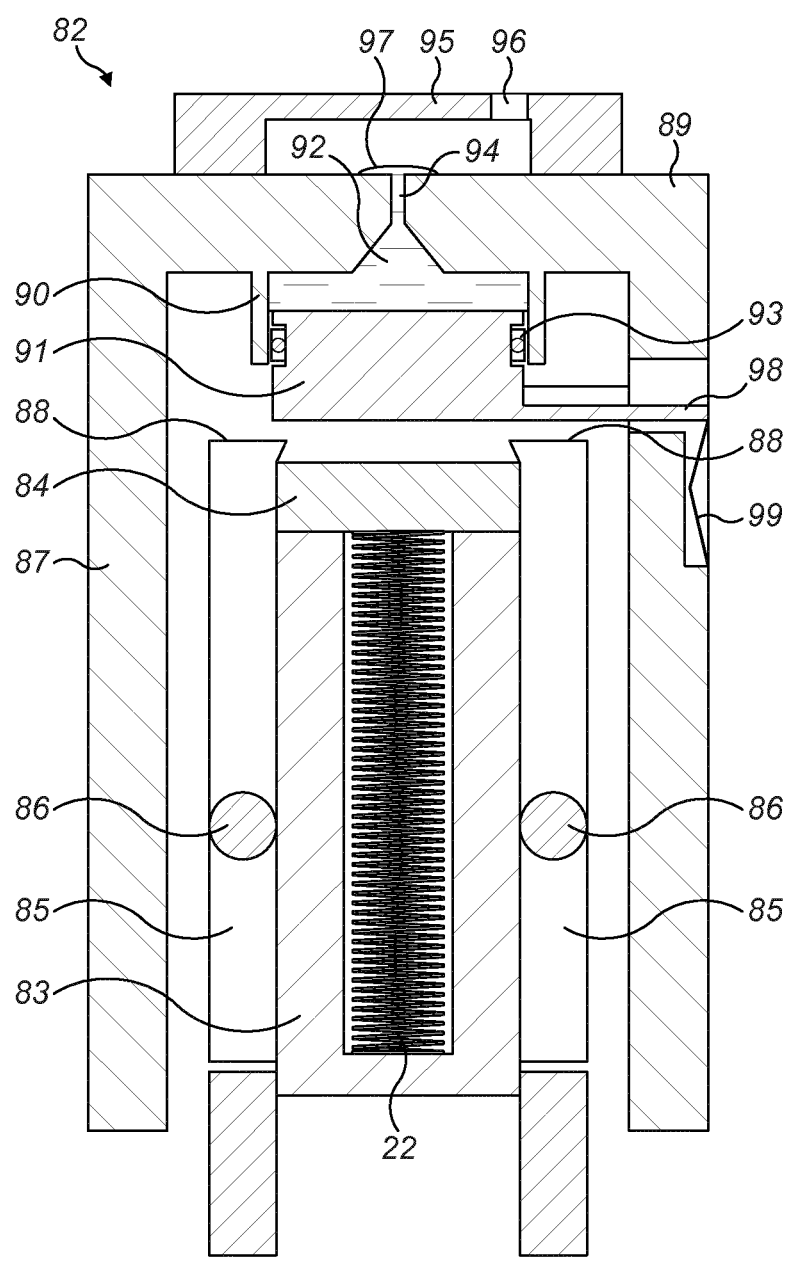
FIG. 7A is a cross-sectional side view of another injection device having a damper and an indicator, shown before the injection device has been used; and, FIG. 7B is a cross-sectional side view of the injection device of FIG. 6A, after the injection device has been used.
Figure 7B:
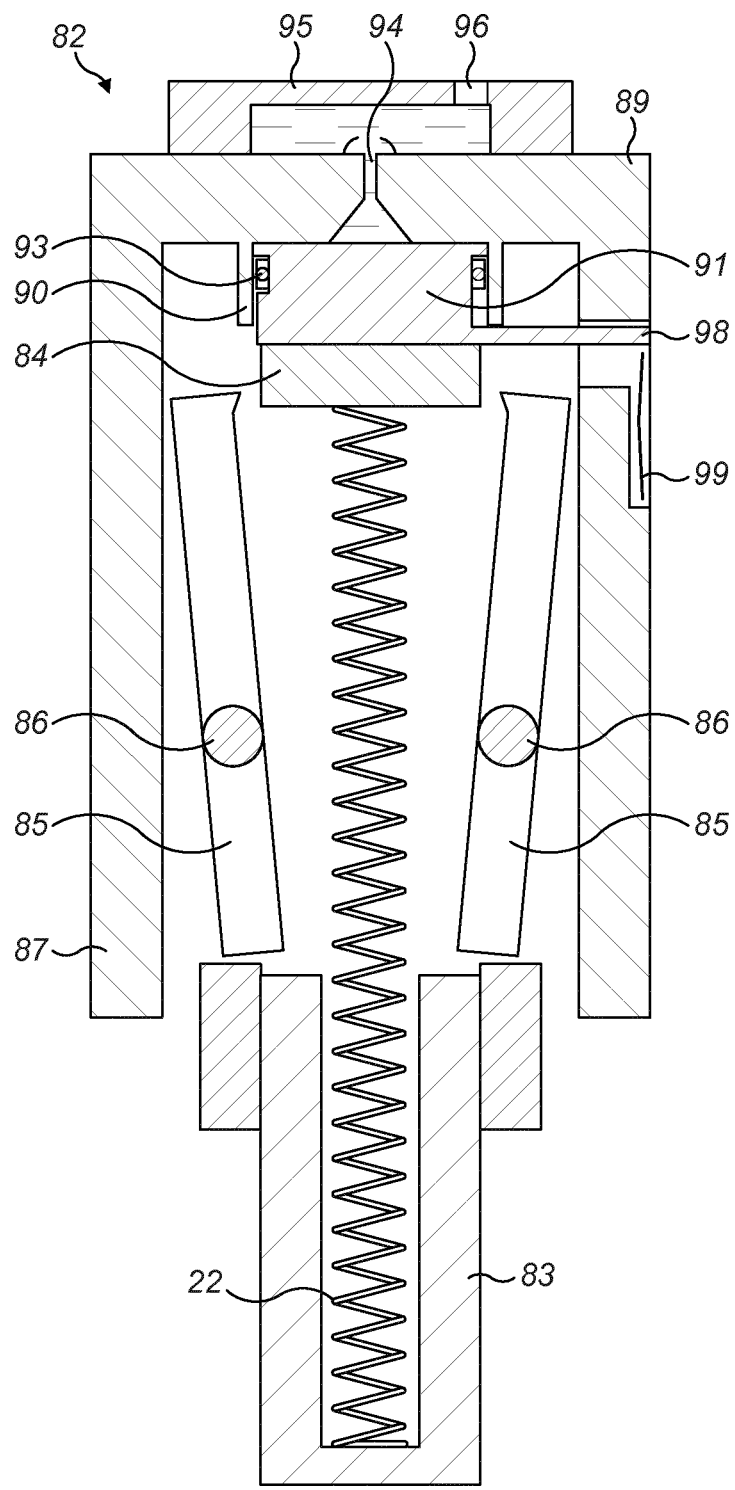

FIG. 7A and FIG. 7B show a further example injection device 82. The injection device 82 includes a plunger 83, a carrier 84, and rotatable locking arms 85 that hold the carrier 84 until the plunger 83 has been moved a distance into the syringe (not shown). As shown in FIG. 7B, once the carrier 84 is released the drive spring 22 urges the carrier 84 in a proximal direction.

The locking arms 85 are pivotally mounted to the housing 87 of the injection device 82 at pivots 86. The locking arms 85 include deflected ends 88 that hold the carrier 84 as the drive spring 22 pushes against the carrier 84. In the initial position, shown in FIG. 7A, the locking arms are prevented from rotating by the presence of the plunger 83. As shown in FIG. 7B, once the drive spring 22 has moved the plunger 83 into the syringe (not shown), the arms 83 can rotate and release the carrier 84.

In this example, the proximal end 89 of the housing 87 has a cylindrical protrusion 90 and a piston 91 is provided within the cylindrical protrusion 90 to define a fluid chamber 92. A seal 93 is provided between the piston 91 and the cylindrical protrusion 90. The proximal end 89 of the housing 87, within the cylindrical protrusion 90, includes an orifice 94. A second chamber 95 is provided on the opposite side of the orifice 94 to the fluid chamber 92. The second chamber 95 is optionally provided with an air outlet 96.

As shown in FIG. 7B, when the carrier 84 is released by the locking arms 84, after the plunger 83 has moved distally, the drive spring 22 urges the carrier 84 against the piston 91, which is pushed into the fluid chamber 92 and urges fluid through the orifice 94 and into the second chamber 95. Air may be displaced from the second chamber 95 through the air outlet 96.

A seal 97 may initially be provided over the orifice 94 to prevent movement of the fluid into the second chamber 95 before the carrier 84 has been released.

The second chamber 95 may additionally be transparent, so that the user can see the fluid entering the second chamber 95 as an indication that the plunger 83 has completed its movement into the syringe (not shown). The fluid may be coloured. The fluid may be a liquid, for example water.

The orifice 94 damps movement of the piston 91 into the fluid chamber 92.

As illustrated in FIG. 7A and FIG. 7B, the piston 91 may trigger an audible indication to the user. In this example, the piston 91 comprises an arm 98 that protrudes from the piston 91 and engages a sound generator. The sound generator is a pre-stressed element 99 that is held in a deflected position by the arm 98 until the piston 91 moves into the fluid chamber 92, at which point the arm 98 disengages the pre-stressed element 99, which returns to its natural shape. This changing of shape of the pre-stressed element 99 generates an audible sound, which provides the user with an indication that enough time has elapsed for the medicament to have dispersed from the injection site. In particular the arm 98 does not disengage the pre-stressed element 99 until a volume of fluid has passed into the second chamber 95, which is delayed by the damping action of the orifice 94, thereby providing a delay in the feedback. The duration of the delay may be, for example, more than 2 seconds, or more than 5 seconds, or more than 10 seconds, or between 10 and 30 seconds, or between 10 and 20 seconds.

The locking arms 85 only release the carrier 84 after the plunger 83 has been moved a pre-determined distance into the syringe (not shown), and the arrangement of the piston 91, fluid chamber 92 and pre-stressed element 99 then creates a further delay before the audible indication is generated, providing time for the medicament to disperse from the injection site.

In any of the above-described injection devices it will be appreciated that the drive spring may be omitted if the injection device is adapted to be manually operated. For example, the injection device may be provided with a lever or button that the user manually operates to push the plunger into the syringe. In this case, the force provided by the user may be used to compress the fluid reservoir.

In any of the above-described examples, the damping effect that provides the delay before the feedback is generated may be increased by using a highly viscous, or non-Newtonian fluid. This reduces the rate at which the fluid can pass through the outlet during compression of the fluid reservoir.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin; B29-N-(N-lithocholyl-gamma-glutamyl)-des(B30) human insulin; B29-N-(ω-carboxyheptadecanoyl)-des(B30) human insulin and B29-N-(ω-carboxyhepta-decanoyl) human insulin. Exemplary GLP-1, GLP-1 analogues and GLP-1 receptor agonists are, for example: Lixisenatide/AVE0010/ZP10/ Lyxumia, Exenatide/Exendin-4/Byetta/Bydureon/ITCA 650/AC-2993 (a 39 amino acid peptide which is produced by the salivary glands of the Gila monster), Liraglutide/ Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present invention, which encompass such modifications and any and all equivalents thereof.

The invention claimed is:

1. An injection device comprising:
 a medicament delivery mechanism comprising:
  a reservoir; and
  a plunger that moves to displace medicament from the reservoir for delivery to a user during use of the injection device; and
 a feedback mechanism comprising:
  a piston;
  a fluid chamber, wherein the piston is configured to move into the fluid chamber during use of the injection device;
  a damper configured to damp movement of the piston; and
  an indicator configured to provide feedback to the user after the piston has moved a predetermined distance into the fluid chamber,
 wherein the piston is configured to move into the fluid chamber after the plunger has moved a predetermined distance into the reservoir, and
 wherein the injection device further comprises at least one locking arm configured to hold the piston until the plunger has reached a predetermined position, the at least one locking arm configured to release the piston after the plunger has reached the predetermined position such that the piston can move into the fluid chamber.

2. The injection device of claim 1, further comprising a biasing member configured to push the plunger into the reservoir during use.

3. The injection device of claim 2, wherein the biasing member is configured to act on the piston, and wherein the piston and plunger are arranged such that force applied to the piston is transferred to the plunger via the fluid chamber.

4. The injection device of claim 1, wherein the damper comprises an orifice.

5. The injection device of claim 1, further comprising a housing, and wherein the damper comprises an orifice formed in the housing.

6. The injection device of claim 5, wherein the indicator comprises a pre-stressed element configured to generate an audible sound when deflected, the pre-stressed element being mounted to the plunger and configured to be deflected as the plunger moves to displace medicament.

7. The injection device of claim 1, wherein the reservoir contains the medicament.

8. A method of using an injection device, the method comprising:
 delivering a medicament to a user;
 moving a piston into a fluid chamber;
 damping the movement of the piston; and
 providing feedback to the user after the piston has moved a predetermined distance into the fluid chamber,
 wherein the piston is configured to move into the fluid chamber after a plunger has moved a predetermined distance into a reservoir, and
 wherein the injection device comprises at least one locking arm configured to hold the piston until the plunger has reached a predetermined position, the at least one locking arm configured to release the piston after the plunger has reached the predetermined position such that the piston can move into the fluid chamber.

* * * * *